US010682501B2

(12) United States Patent
Rollins et al.

(10) Patent No.: US 10,682,501 B2
(45) Date of Patent: Jun. 16, 2020

(54) SYSTEM AND METHOD FOR TRAVERSING AN ARTERIAL OCCLUSION

(71) Applicant: VESATEK, LLC, Irvine, CA (US)

(72) Inventors: Aaron Rollins, Miami Beach, FL (US); Tor Alden, Basking Ridge, NJ (US); Russell Roy Lyon, Days Creek, OR (US)

(73) Assignee: Vesatek, LLC, Irvine, CA (US)

( * ) Notice: Subject to any disclaimer, the term of this patent is extended or adjusted under 35 U.S.C. 154(b) by 694 days.

(21) Appl. No.: 15/368,517

(22) Filed: Dec. 2, 2016

(65) Prior Publication Data

US 2017/0080190 A1 Mar. 23, 2017

Related U.S. Application Data

(60) Continuation of application No. 14/806,473, filed on Jul. 22, 2015, now Pat. No. 9,539,416, which is a
(Continued)

(51) Int. Cl.
*A61M 25/09* (2006.01)
*A61B 17/3207* (2006.01)
*A61B 17/22* (2006.01)

(52) U.S. Cl.
CPC .......... *A61M 25/09041* (2013.01); *A61B 17/320758* (2013.01); *A61B 2017/22038* (2013.01);
(Continued)

(58) Field of Classification Search
CPC ...... A61M 25/09041; A61M 2205/103; A61M 2205/106; A61M 2025/09116; A61B 17/320758; A61B 2017/22038
See application file for complete search history.

(56) References Cited

U.S. PATENT DOCUMENTS 3,748,435 A 7/1973 Reynolds
3,847,140 A 11/1974 Ayella
(Continued)

FOREIGN PATENT DOCUMENTS

EP 0442137 B1 2/1996
JP H03-5635 8/1992

OTHER PUBLICATIONS

European Search Report for Application 10741626.5, dated Jul. 30, 2013, 6 pages.
(Continued)

*Primary Examiner* — Devin B Henson
(74) *Attorney, Agent, or Firm* — Blair Walker IP Services, LLC

(57) ABSTRACT

A system for traversing an arterial occlusion in an artery includes a housing sized to fit in a palm of a user, an elongate drive tube configured to be rotated by the housing, the drive tube including an axially extending passage, a cylindrical member, configured to be rotationally coupled to the drive tube, such that a distal tip of the cylindrical member may be delivered to a location adjacent the arterial occlusion when the cylindrical member is coupled to the drive tube, and wherein grasping and activating the housing such that the drive tube is rotated, thereby causes the distal tip of the cylindrical member to be rotated, the rotation of the distal tip including at least a component of linear oscillation.

18 Claims, 9 Drawing Sheets

Related U.S. Application Data division of application No. 14/559,874, filed on Dec. 3, 2014, now Pat. No. 9,119,941, which is a continuation of application No. 12/658,629, filed on Feb. 9, 2010, now Pat. No. 8,926,529.

(60) Provisional application No. 61/151,388, filed on Feb. 10, 2009.

(52) U.S. Cl.
CPC .............. *A61M 2025/09116* (2013.01); *A61M 2205/103* (2013.01); *A61M 2205/106* (2013.01); *A61M 2210/12* (2013.01)

(56) References Cited

U.S. PATENT DOCUMENTS

| | | | |
|---|---|---|---|
| 4,030,503 A | 6/1977 | Clark, III | |
| 4,854,325 A | 8/1989 | Stevens | |
| 5,055,109 A | 10/1991 | Gould et al. | |
| 5,158,564 A | 10/1992 | Schnepp-Pesch et al. | |
| 5,195,954 A | 3/1993 | Schnepp-Pesch et al. | |
| 5,243,997 A | 9/1993 | Uflacker et al. | |
| 5,318,529 A | 6/1994 | Kontos | |
| 5,325,868 A | 7/1994 | Kimmelstiel | |
| 5,327,906 A | 7/1994 | Fideler | |
| 5,389,072 A | 2/1995 | Imran | |
| 5,392,778 A | 2/1995 | Horzewski | |
| 5,443,078 A | 8/1995 | Uflacker | |
| 5,507,738 A | 4/1996 | Ciervo | |
| 5,524,180 A | 6/1996 | Wang et al. | |
| 5,524,635 A | 6/1996 | Uflacker et al. | |
| 5,634,475 A | 6/1997 | Wolvek | |
| 5,660,180 A | 8/1997 | Malinowski et al. | |
| 5,709,661 A | 1/1998 | Van Egmond et al. | |
| 5,735,535 A | 4/1998 | McCombs et al. | |
| 5,766,191 A | 6/1998 | Trerotola | |
| 5,893,857 A | 4/1999 | Shturman et al. | |
| 5,908,395 A | 6/1999 | Stalker et al. | |
| 5,911,722 A | 6/1999 | Adler et al. | |
| 6,027,460 A | 2/2000 | Shturman | |
| 6,165,188 A | 12/2000 | Saadat et al. | |
| 6,179,809 B1 | 1/2001 | Khairkhahan et al. | |
| 6,183,432 B1 | 2/2001 | Milo | |
| 6,348,040 B1 | 2/2002 | Stalker et al. | |
| 6,394,976 B1 * | 5/2002 | Winston .......... | A61M 25/09041 604/95.04 |
| 6,533,772 B1 | 3/2003 | Sherts et al. | |
| 6,544,231 B1 | 4/2003 | Palmer et al. | |
| 6,551,302 B1 | 4/2003 | Rosinko et al. | |
| 6,554,794 B1 | 4/2003 | Mueller et al. | |
| 6,726,675 B1 | 4/2004 | Beyar | |
| 6,752,800 B1 | 6/2004 | Winston et al. | |
| 7,615,042 B2 | 11/2009 | Beyar et al. | |
| 7,766,894 B2 | 8/2010 | Weitzner et al. | |
| 8,142,458 B2 | 3/2012 | Shturman | |
| 8,187,229 B2 | 5/2012 | Weitzner et al. | |
| 8,323,239 B2 | 12/2012 | Bednarek et al. | |
| 8,500,697 B2 | 8/2013 | Kurth et al. | |
| 8,852,219 B2 | 10/2014 | Wulfman et al. | |
| 2002/0177789 A1 | 11/2002 | Ferry et al. | |
| 2003/0040694 A1 | 2/2003 | Dorros et al. | |
| 2003/0088187 A1 | 5/2003 | Saadat et al. | |
| 2003/0216760 A1 | 11/2003 | Welch et al. | |
| 2004/0054322 A1 | 3/2004 | Vargas | |
| 2004/0236214 A1 | 11/2004 | Opie et al. | |
| 2005/0240116 A1 | 10/2005 | Saadat et al. | |
| 2005/0240120 A1 | 10/2005 | Modesitt | |
| 2005/0244521 A1 | 11/2005 | Strickland et al. | |
| 2005/0277851 A1 | 12/2005 | Whittaker et al. | |
| 2006/0041245 A1 | 2/2006 | Ferry et al. | |
| 2006/0074442 A1 | 4/2006 | Noriega et al. | |
| 2006/0184186 A1 | 8/2006 | Noone | |
| 2006/0229587 A1 | 10/2006 | Beyar et al. | |
| 2006/0282150 A1 | 12/2006 | Olson et al. | |
| 2007/0016105 A1 | 1/2007 | Mamourian | |
| 2007/0060879 A1 | 3/2007 | Weitzner et al. | |
| 2007/0167804 A1 | 7/2007 | Park et al. | |
| 2007/0219467 A1 | 9/2007 | Clark et al. | |
| 2007/0225615 A1 | 9/2007 | Chechelski et al. | |
| 2007/0239182 A1 | 10/2007 | Glines et al. | |
| 2007/0270755 A1 | 11/2007 | Von Oepen et al. | |
| 2008/0097465 A1 | 4/2008 | Rollins et al. | |
| 2008/0119824 A1 | 5/2008 | Weitzner et al. | |
| 2008/0255539 A1 | 10/2008 | Booth | |
| 2009/0082722 A1 | 3/2009 | Munger et al. | |
| 2009/0105645 A1 | 4/2009 | Kidd et al. | |
| 2009/0264940 A1 | 10/2009 | Beale et al. | |
| 2010/0174233 A1 | 7/2010 | Kuban et al. | |
| 2010/0217275 A1 | 8/2010 | Carmeli et al. | |
| 2010/0280534 A1 | 11/2010 | Sher | |
| 2012/0071907 A1 | 3/2012 | Pintor et al. | |
| 2012/0078080 A1 | 3/2012 | Foley et al. | |

OTHER PUBLICATIONS

Office Action from Japanese Patent Office for corresponding Japanese application No. P2011-549330, Nov. 11, 2014, 8 pages.

* cited by examiner

SYSTEM AND METHOD FOR TRAVERSING AN ARTERIAL OCCLUSION

CROSS-REFERENCE TO RELATED APPLICATIONS

This application is a continuation of U.S. patent application Ser. No. 14/806,473, filed on Jul. 22, 2015, and incorporated in its entirety by reference herein for all purposes, which is a division of U.S. patent application Ser. No. 14/559,874, filed on Dec. 3, 2014, and incorporated in its entirety by reference herein for all purposes, which is a continuation of U.S. patent application Ser. No. 12/658,629, filed on Feb. 9, 2010 and incorporated in its entirety by reference herein for all purposes, which claims the benefit of priority to U.S. Provisional Appl. No. 61/151,388, filed on Feb. 10, 2009, which is incorporated in its entirety by reference herein for all purposes.

BACKGROUND OF THE INVENTION

Field of the Invention

Embodiments of the present invention generally relate to surgical guidewire utilization in surgical procedures and, more particularly, to a method and apparatus fir manipulating a surgical guidewire.

Description of the Related Art

A surgical guidewire (referred to herein also as a guidewire) is typically semi-rigid probe used as an initial access point for performing in endovascular surgical procedure. The guidewire is twisted, bent, and otherwise maneuvered through an access vessel in order to position the guidewire tip and a location a surgeon desires to treat.

Conventional guidewire manipulation meth ds often involve applying torque to the guidewire to aid its passage through tortuous and dogged vessels. Typically, spinning the guidewire in one's fingertips creates torque to assist in manipulating the guidewire through an obstructed and/or difficult passageway. This technique is also known as "helicoptering", alluding to the spinning blades of a helicopter.

However, applying torque is difficult since surgical guidewires have an extremely small diameter and typically have a low friction surface to promote passage through a vessel. Additionally, the gloves of a surgeon or often coated with blood or saline solution, further increasing the slickness of a guidewire. In this respect, helicoptering and similar maneuvers can be time-consuming and inefficient. This inefficiency not only frustrates surgeons, but also increases procedure completion time and, therefore, increases procedure costs.

Furthermore, in instances where an obstruction is encountered within a vessel, a surgeon generally applies axial motion in an oscillatory manner to drive the guidewire through or past the obstruction. During surgery, an endovascular surgeon may encounter an occlusion that is chronic and/or calcified. Such occlusions have a hard shell with a consistency much like plaster. These forms of obstructions can be difficult and sometimes impossible to penetrate using manual manipulation of a guidewire. Consequently, a procedure may be abandoned when such difficult obstructions are encountered.

Therefore, there is a need in the art for a method and apparatus for manipulating a guidewire.

SUMMARY OF THE INVENTION

Embodiments of the present invention generally comprise a method and apparatus for manipulating a surgical guidewire. Specifically, the apparatus comprises a chuck for selectively coupling motive force to a surgical guidewire and an actuator, coupled to the chuck, for imparting an axial motive force to the chuck. Embodiments of the invention further comprise a method of using the apparatus.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention comprise a method and apparatus for manipulating a surgical guidewire. The method and apparatus are embodied in a guidewire manipulation device for selectively imparting motive force (rotational and/or axial (linear) motion) to a surgical guidewire. In use, such a guidewire manipulation device is selectively locked to a surgical guidewire and is activated to impart motive force to maneuver the guidewire to a desired location during an endovascular procedure. The motive force applied to the guidewire is selectively rotational or axial to facilitate moving the surgical guidewire through a vessel and/or penetrating occlusions.

Figure 1:
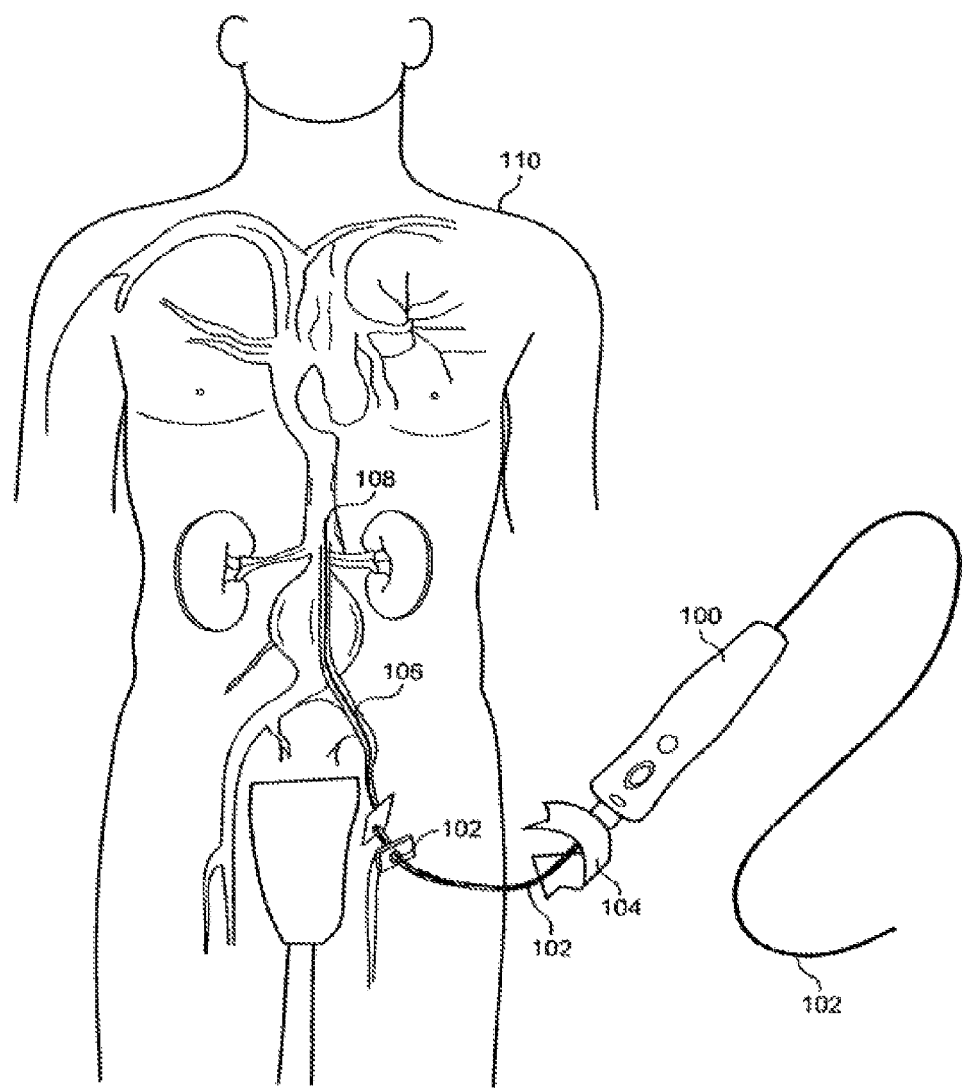
FIG. 1 illustrates a view of one embodiment of a guidewire manipulation device being used on a patient according to an embodiment of the present invention.

FIG. 1 illustrates a view of a guidewire manipulation device 100 being used on a patient 110 according to one embodiment of the present invention. In one embodiment, the guidewire manipulation device 100 is a handheld device capable of fitting in the palm of a uses hand and being operated using one hand. In one embodiment, the guidewire manipulation device 100 is advanced over a surgical guidewire 102, i.e., the guidewire 102 passes through a longitudinally oriented passage in the device 100). During an endovascular procedure, the guidewire 102 is introduced into a vessel 106 (e.g., a femoral artery) of the patient 110. The guidewire manipulation device 100 is selectively locked to the guidewire 102. As the guidewire is advanced into the patient, the user operates the manipulation device 100 to impart motive force (rotational and/or axial motion) to the guidewire 102, as appropriate.

For example, as a distal end 108 of the guidewire 102 reaches an angled or curved region of the vessel 106, the user locks the manipulation device 100 to the guidewire and imparts rotational motive force to the guidewire 102 (e.g., in a counterclockwise direction indicated, by arrow 104), thereby causing the distill end 108 of the guidewire 102 to more easily advance through the angled or curved region of the vessel 106. Once advanced past the region, the device 100 is unlocked from the guidewire and the guidewire can be further advanced through the vessel. In another example, the distal end 108 of the guidewire 102 reaches an obstruction (e.g., an embolism) but is unable to pass the obstruction. The user then locks the guidewire manipulation device 100 to the guidewire 102 and imparts a vibratory motion (e.g., rapidly oscillating between clockwise and counterclockwise rotation). Such motion causes the distal end of the guidewire 102 to pass through the obstruction. In another example, when the distal end of the guidewire 102 reaches an obstruction, the user locks the guidewire manipulation device 100 to the guidewire 102 and imparts an axial motion (e.g., a linear movement of the guidewire 102) to create a jackhammer effect. In another embodiment, the user may lock the device 100 to the guidewire 102 and simultaneously impart both rotational and axial motion to the guidewire 102. In another embodiment of the invention, a sequence of pre-defined guidewire manipulations (i.e., a pattern) may be produced using a computer program for controlling the motion as described in detail below. Various motive patterns to be selectively used in various surgical situations can be selected from memory and applied to the guidewire.

Figure 2:
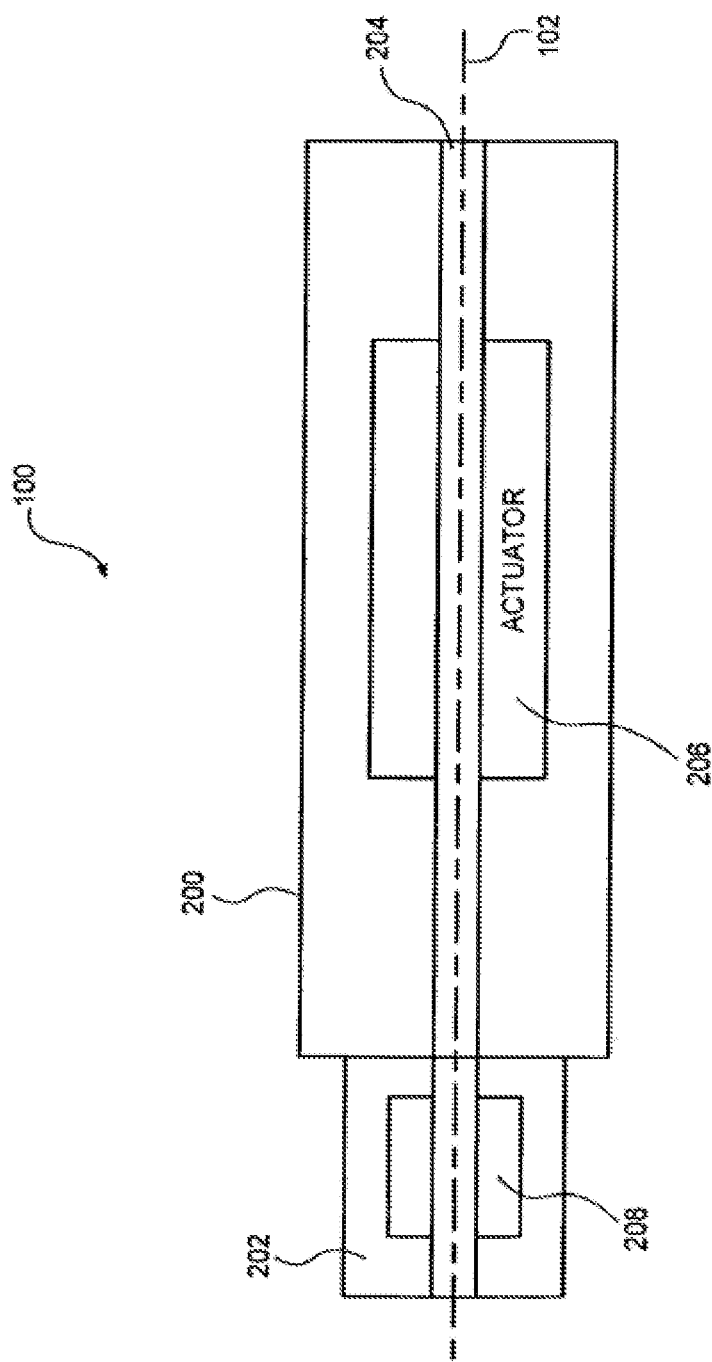
FIG. 2 depicts a schematic block diagram of a guidewire manipulation device according to an embodiment of the present invention.

FIG. 2 depicts a schematic block diagram of one embodiment of a guidewire manipulation device 100. The guidewire manipulation device 100 defines an axially longitudinal passage 204 through which the guidewire 102 is threaded during use. The guidewire manipulation device 100 comprises a housing 200, an actuator 206, and a chuck 202. The chuck 202 comprises a guidewire locking mechanism 208. During use, the chuck 202 is locked to the guidewire 102 using the locking mechanism 208. Once locked, the actuator selectively imparts motive force (rotational motion and/or axial motion) to the guidewire 102.

Figure 3:
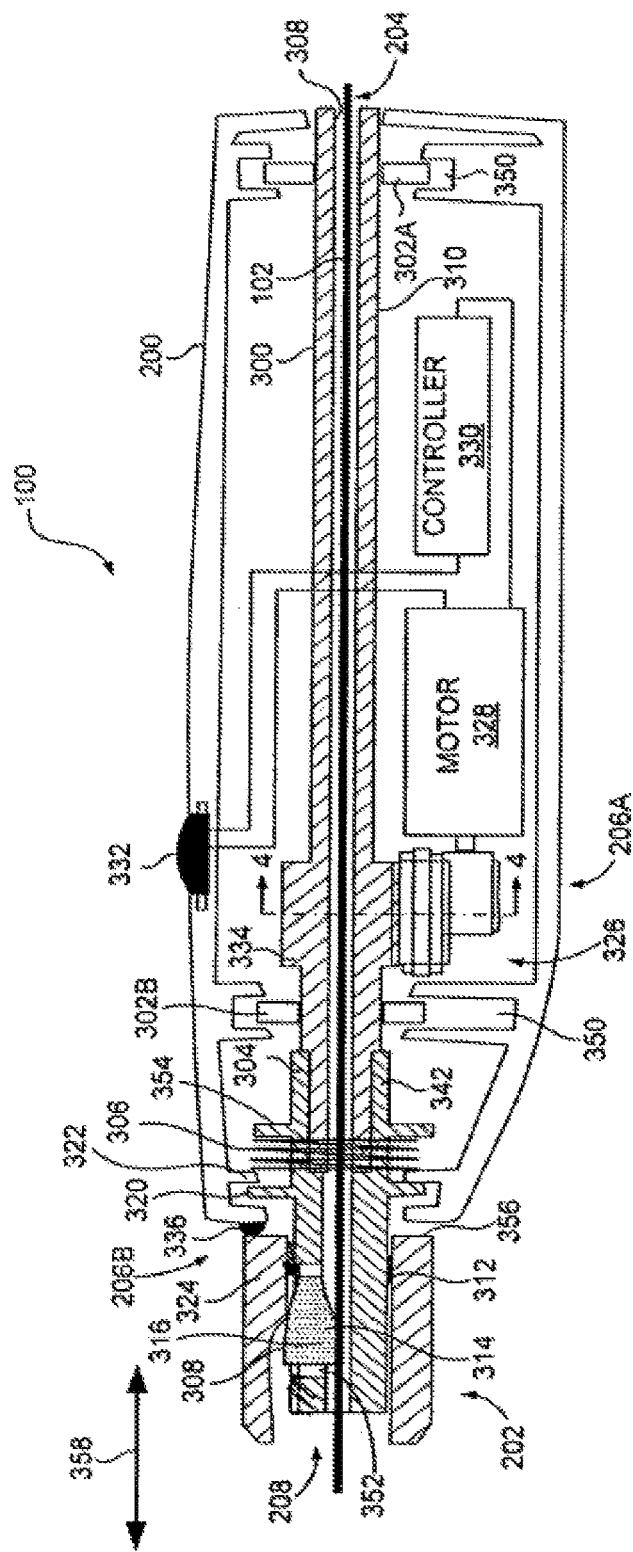
FIG. 3 depicts a vertical cross-sectional view of a guidewire manipulation device according to an embodiment of the present invention.

FIG. 3 depicts a vertical cross-sectional view of one embodiment of a guidewire manipulation device 100. In this embodiment, the actuator 206 of FIG. 2 is divided into a rotary actuator 206A and an axial actuator 206B such that the device may selectively apply to the guidewire: no motive force, rotary motive force or rotary and axial motive force.

Device 100 comprises a housing 200 typically formed into halves that are glued, screwed, or otherwise affixed to each other to form an enclosure. Within the housing 200 are defined slots 350 wherein are retained bushings 302A and 302B. The bushings 302A and 302B support an axle 300. The axle 300 defines the passage 204 extending axially through the axle 300. When in use, the guidewire 102 is threaded through the passage 204.

The rotary actuator 206A comprises the axle 300, a motor 328, a drive assembly 326, a controller 330, and a control switch 332. The drive assembly 326 couples rotational motion of the motor 328 to the axle 300 using a plurality of gears, further described with respect to FIG. 4 below, in one embodiment of the Invention, the controller 330 is simply one or more batteries that are coupled to the motor 328 via the control switch 332. In such an embodiment, the control switch 332 may simply apply a voltage from the one or more batteries to the motor 328 to cause the motor 328 to rotate. In its simplest form, the control switch 332 is a simple single-pole, single-throw (SPST), momentary contact switch. In more complex embodiments, the controller 330 comprises a programmable microcontroller as described with respect to FIG. 6 below. In other embodiments, the switch 332 may apply voltage to cause the motor 328 to selectively rotate clockwise or counterclockwise. The control switch 332 is generally mounted to be exposed to the exterior of the housing 200 and facilitate manipulation by one hand of a user (e.g., a thumb activated push-button or slide switch.

The axle 300 is coupled to a chuck 202. In one embodiment, the chuck 202 comprises a coupler 304, a hub 324 and a wedge 314. The coupler 304 and the axle 300 have splined mating surfaces 342 for coupling the rotational motion of the axle 300 to the chuck 202, while allowing the coupler 304 to move in an axial direction. The hub 324 is threaded onto the coupler 304 at surface 312. The wedge 314 is located in a window 352 defined by the coupler 304. The hub 324 retains the wedge 314 within the window 352. In a disengaged (unlocked) position, the hub 324 does not impart pressure to the wedge 314 thereby allowing the guidewire 102 to slide freely beneath the wedge 314 and through the passage 204. To lock the guidewire into the lock mechanism 208, the hub 324 is rotated relative to the coupler 304 such that the angled surface 316 of the hub 324 interacts with the top surface 308 of the wedge 314. As the hub 324 is moved relative to the coupler 304 via the mating threaded surfaces 312, the wedge 314 its forced against the guidewire 102. Consequently, the guidewire is captured between the wedge 314 and the coupler 304 and thereby locked into the chuck 202. Once locked, any motion of the chuck 202 is imparted as motive force to the guidewire 102.

Other embodiments of the invention utilize other forms of chucks. In a broad sense, any mechanism that can be used to selectively lock the guidewire to a source of motive force may be used. Other forms of chucks having multiple saws or compressive slotted cylinders are applicable.

The coupler 304 comprises a spring seat 354 supporting a first end of a spring 306. The second end of spring 306 rests against a flange 322 that extends from the inner surface of the housing 200. The spring 306 is one embodiment of a resilient member that biases the coupler 304 inwardly toward the axle 300. The coupler 304 further comprises a flange 320 that extends radially from the outer surface of the coupler 304. The flange 320 is positioned along the coupler 304 to limit the amount of axial movement that can be imparted to the chuck 202. The flange 320 abuts the housing flange 322. As such, the spring 30 biases the coupler 304 to maintain contact between the flange 320 and the flange 322.

To impart axial motion to the chuck 202, the bottom surface 356 of the hub 324 is dimpled. The surface 356 interacts with a protrusion 335 extending from the exterior surface of the housing 200 proximate the surface 356 of the hub 324. Depending on the position of the hub 324 relative to the coupler 304, the spring 306 insurers that the protrusion 338 interacts with the dimpled surface 356. Upon locking the chuck 202 to the guidewire 102 and imparting rotation to the chuck 202, the guidewire 102 moves in an axial direction as indicated by arrow 358. To disengage the axial motive force, the hub 324 is rotated relative to the coupler 304 along the threads 312 to decouple the protrusion 336 from the surface 356. In this manner, the locking mechanism 208 retains the guidewire 102 such that rotational motion of the axle 300 is imparted to the guidewire 102 without imparting axial motion. In this embodiment, the axial motion actuator 206B comprises the hub 324, spring 306, coupler 304 and the housing 200.

Figure 4:
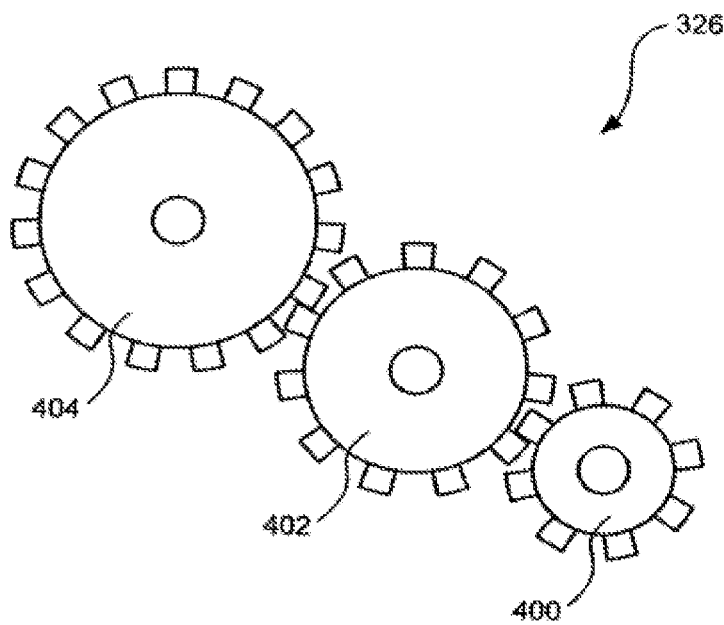
FIG. 4 depicts a portion of an actuator used in the guidewire manipulation device of FIG. 3.

FIG. 4 depicts a cross sectional view of the drive assembly 326 of the rotary actuator 206A taken along line 4-4 of FIG. 3 in accordance with one embodiment of the invention. The drive assembly 326 comprises a motor gear 400, an intermediary gear 402 and an axle gear 404. The motor 328 of FIG. 3 is coupled to the motor gear 400 to impart rotational motion to the motor gear. In one embodiment, the axle gear 404 is formed as an integral part of this surface of the axle 300 of FIG. 3. The intermediary gear 402 is designed to provide a gear ratio between the motor gear 400 and axle gear 404. The diameters and the number of teeth of each gear is considered to be a design choice that will do fine the speed of rotational motion of the guidewire as well as the oscillatory speed of the axial motion.

In other embodiments, the motor 328 of FIG. 3 may be coupled to the axle via other forms of drive assemblies, e.g., direct drive, worm gear, and/or the like. The specific motor and drive assembly characteristics are considered a design choice to develop specific guidewire rotation speed and torque. In some embodiments, the drive assembly may be adjustable to facilitate creating specific speed and torque profiles or adjustments. One form of adjustments may be facilitated by the use of a stepper motor that can be controlled with a pulse width modulated signal produced by the controller, as discussed below.

An alternative embodiment for imparting rotary motive force in selectable directions uses a gear train comprising two larger diameter spur gears mounted on a common shaft that is driven constantly in one direction by an electric motor. Each of the two spur gears has a section of its teeth, something over ½ its total number, removed. The removed sections of teeth are positioned such that only one or the other of two additional smaller spur gears, each located to be driven by one of these common shaft gears, will be driven at a time; The two smaller spur gears are then used one at a time to drive the gear on the axle, but the positioning of one additional gear between just one of these driving gears and the axle gear results in the rotational direction of the axle being reversed when that set is driving the axle gear.

Another embodiment, if only forward and reversing is required without a near constant rotational speed in either direction, has the spur gear on the axle driven by a pivoted ¼ pie shaped plate. The toothed curved section opposite the pivot near the tip would have the correct pitch radius to mesh with the axle spur gear. This pivoted gear section plate would have, running upwards from its pivot, a slot in its face in which a pin, mounted off-center on a disc, could slide up and down freely. As an electric motor turns this disc in a constant direction, it would cause the pivoted plate to wobble back and forth so that its gear section drives the axle spur gear in one direction and then in the reverse direction.

Figure 5:
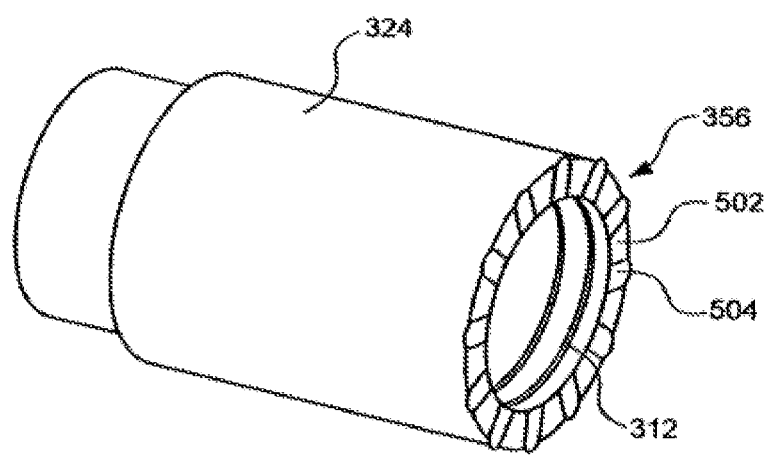
FIG. 5 depicts a perspective view of a hub of a chuck that imparts axial motive force to a guidewire when using the guidewires manipulation divisive FIG. 3.

FIG. 5 depicts a perspective view of the hub 324 in accordance with one embodiment of the invention. The hub 324 comprises a surface 356 having a plurality of dimples 504 and spaces 502 between the dimples 504. The hub 324 further comprises a threaded interior surface 312. The threaded interior surface 312 is adapted to interact with a threaded exterior surface of the coupler 304 to adjust the position of the hub relative to the coupler 304 and the wedge 314. The dimples 504 and the spaces 502 between the dimples 504 are adapted to interact with the protrusion 336 to impart axial motion to the chuck 202. The spacing of the dimples and the speed of the motor control the oscillation rate of the axial motion. Furthermore, the depth of the dimples 504 relative to the spaces 502 on the surface 356 controls the travel distance of the axial motion.

Figure 6:
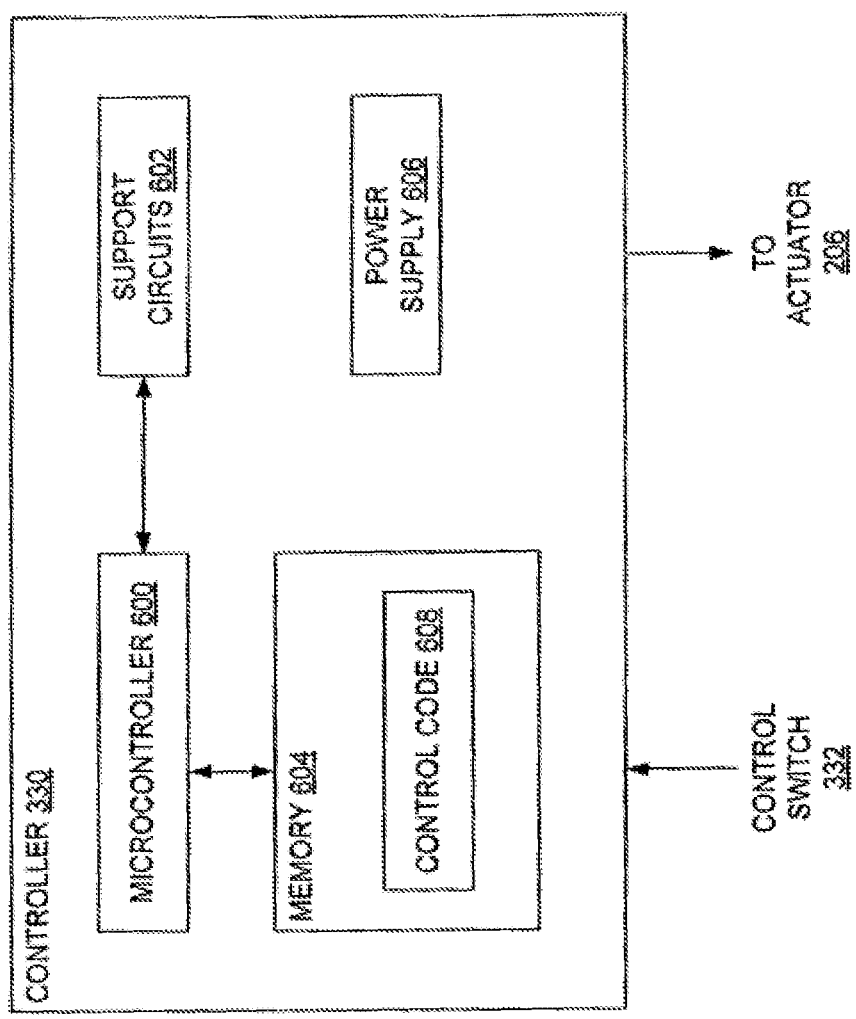
FIG. 6 depicts a block diagram of a controller for a guidewire manipulation device in accordance with an embodiment of the present invention.

FIG. 6 depicts a block diagram of the controller 330 in accordance with one embodiment of the present invention. The controller 330 comprises a microcontroller 600, support circuits 602, memory 604 and a power supply 606. The microcontroller 600 may be one or more of many commercially available microcontrollers, microprocessors, application specific integrated circuits (ASIC), and the like. The support circuits 602 comprise well known circuits that facilitate the operation of the microcontroller 600 including, but not limited to, clock circuits, cache, power supplies, input/output circuits, indicators, sensors, and/or the like. In one embodiment, the power supply 606 comprises one or more batteries. In other embodiments, the power supply 606 may comprise in AC to DC converter to allow the guidewire manipulation device to be plugged into a wall socket. In further embodiments, the power supply 606 may comprise one or more batteries and a charging circuit for the batteries may be inductively coupled to a base charger.

The memory 604 may be any form of memory device used to store digital instructions for the microcontroller 600 as well as data. In one embodiment, the memory 604 is random access memory or read only memory comprising control code 608 (e.g., computer readable instructions) that are used to control the actuator 206 to impart motion to the guidewire. The programs utilized by the microcontroller 600 to control the actuator 206 are generally controlled by the control switch 332 and/or another input device.

In one embodiment of the invention, the motor 328 is a stepper motor that is controlled using, for example, a pulse width modulated signal produced by the controller 330 to impart specific torque and/or speed profiles to the motor 328. In some embodiments, predefined programs can be generated and selected through manipulation of the switch 332 to enable a user to overcome specific types of obstructions within the path of the guidewire. For example, if a surgeon encounters a specific type of embolism, a specific program defining the motion of the guidewire to overcome the obstruction can be selected and implemented. Various programs can be generated through empirical study of guidewire utilization in endovascular procedures. To select a particular motion pattern, the switch may be a slide switch having a plurality of selectable positions, where each position corresponds to a different motion pattern.

Figure 7:
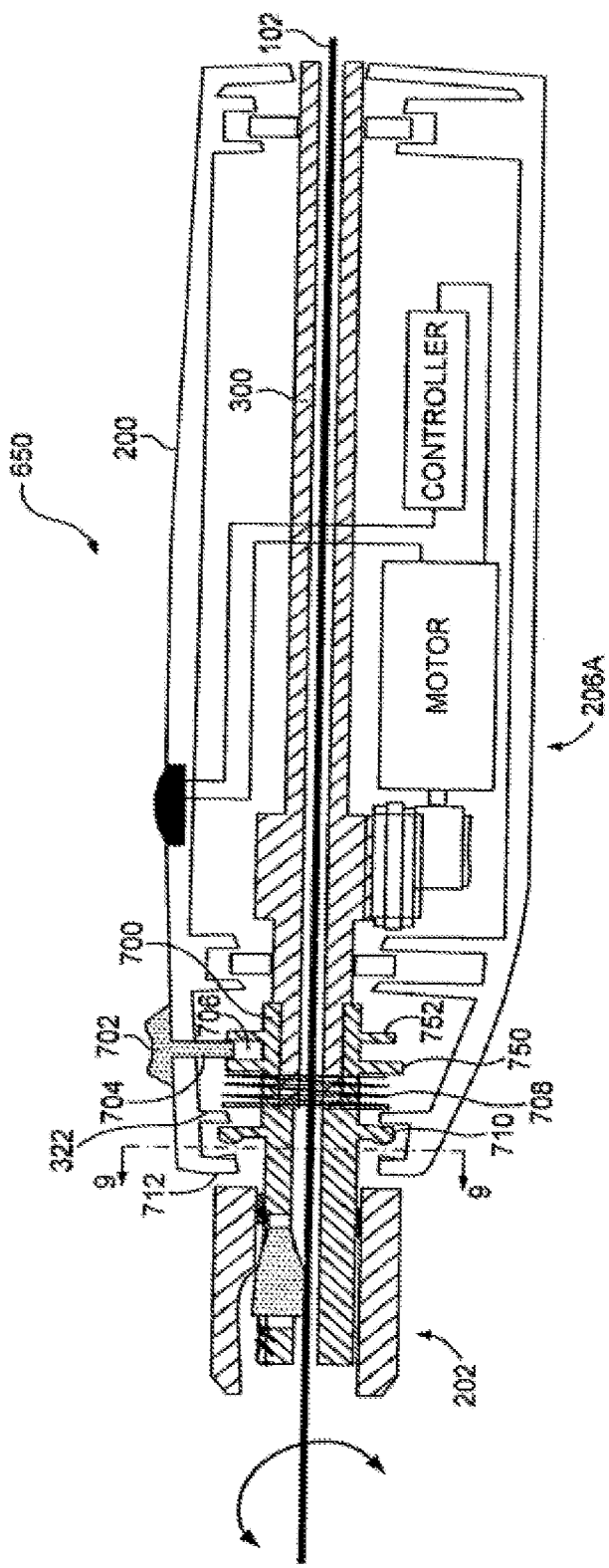
FIG. 7 depicts a vertical cross-sectional view of alternative embodiment of the guidewire manipulation device.

FIG. 7 depicts a vertical cross-sectional view of a guidewire manipulation device 650 according to an alternative embodiment of the invention. In this embodiment, the use of axial motion is selected through manipulation of a mechanical switch 702. As with the prior embodiment, this embodiment selectively imparts to a guidewire: no motive force, rotary motive force, or rotary and axial motive force. The device 650 comprises a rotational actuator 206A as described above with respect to FIG. 3. In this embodiment, a coupler 700 comprises a spring seat 750, a dimpled flange 710 and a switch stop 752. A slidable switch 702 comprises an extension 704 that interacts with a switch seat 752. The switch seat 752 and the spring seat 750 define a space 706 that captures the switch extension 704. Manipulation of the switch 702 causes the coupler 700 to move axially along the surface that mates with the axle 300. A spring 708 is positioned between the spring seat 750 and the housing flange 322. The spring 708 biases the coupler 700 inwardly toward the axle 300. The dimpled flange 710 radially extends from the coupler 700. One surface of the dimpled flange 710 abuts the housing flange 322 to limit the distance the coupler 700 moves in an axial direction. The dimpled flange 710 has a surface aligned with a dimpled surface 712 of the housing 200. When the guidewire is locked to the chuck 202 and the rotational actuator 206A is activated, the guidewire 102 rotates without any axial movement. As described further with respect to FIG. 10 below, when the switch 702 is moved forward to cause the dimpled surface of flange 710 to engage the dimpled surface 712, the guidewire 102 axial motive force is imparted to the guidewire 102.

Figure 8:
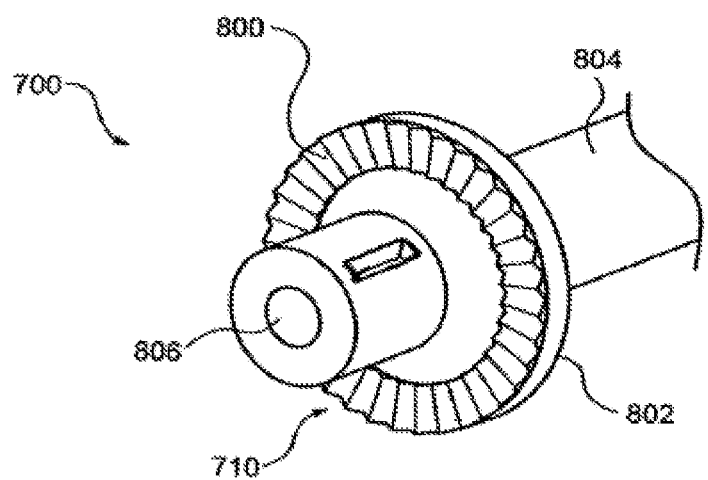
FIG. 8 depicts a partial perspective view of a portion a guidewire drive assembly for the guidewire manipulation device of FIG. 7.

FIG. 8 depicts a partial perspective view of the coupler 700 in accordance with one embodiment of the invention. The coupler 700 has an aperture 806 through which the guidewire is threaded. The dimpled flange 710 comprises a radially extending flange 802 having a plurality of dimples 800 formed in the surface. In one embodiment, the dimples are formed as a sequence of wedges. In other embodiments, to cause axial motion of the chuck when the coupler 700 is rotated, the surface of the flange 802 needs to be varied such that interaction with a corresponding surface causes axial movement of the coupler 700.

Figure 9:
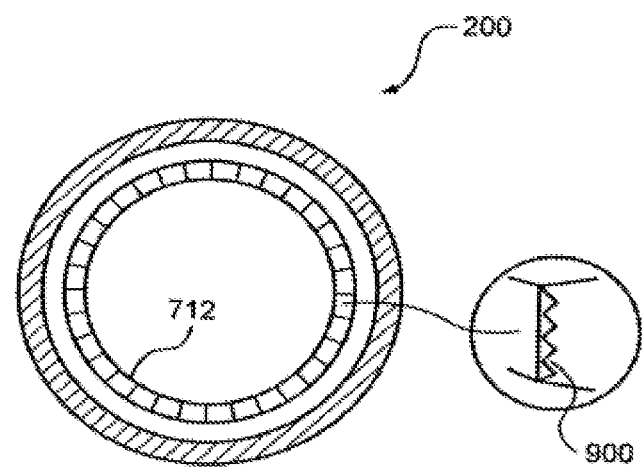
FIG. 9 depicts a cross-sectional view of urine for the guidewire manipulation device of FIG. 7.

FIG. 9 depicts a cross-sectional view of the housing 200 taken along line 9-9 in FIG. 7. In one embodiment, the surface 712 comprises corresponding protrusions shaped to interact with the dimples in surface 800 of the coupler 700. In another embodiment, the surface 712 may comprise complementary wedges 900 to the surface 800 of the coupler 700. The shape of the wedges defines, in part, the distance traveled, the rate of acceleration of the guidewire, and the speed of the guidewire oscillation.

Figure 10:
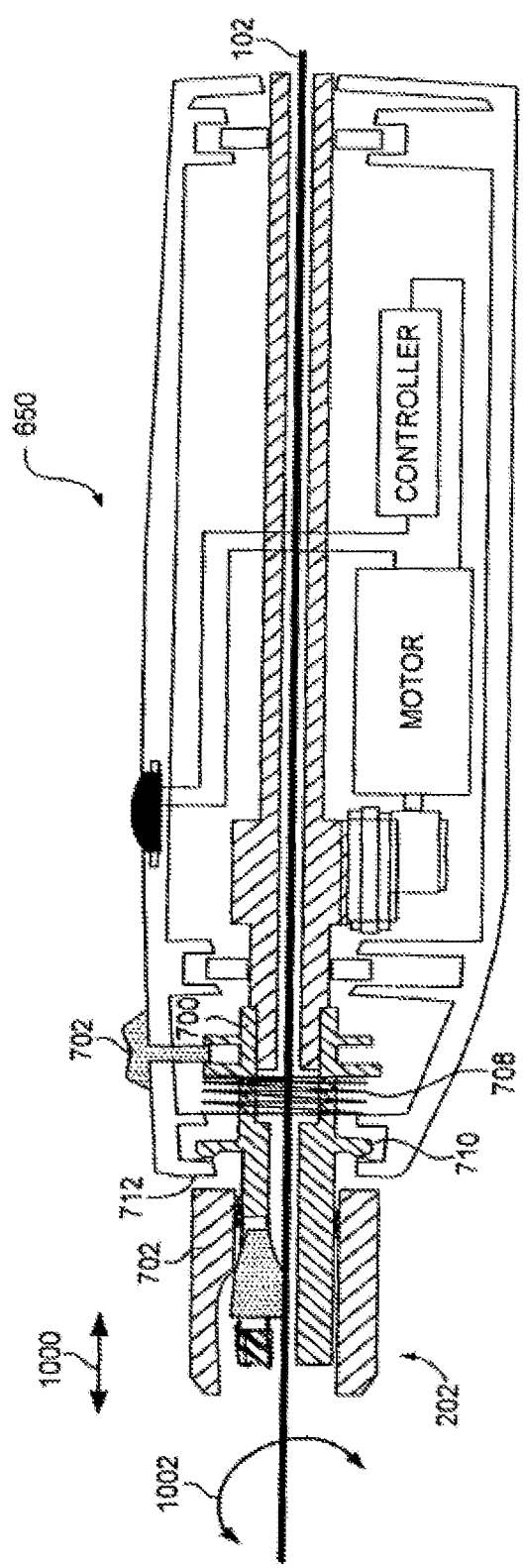
FIG. 10 depicts a vertical cross-sectional view of the guidewire manipulation device of FIG. 7 having the actuator engaged to apply axial motive force to the guidewire in accordance with one embodiment of the invention.

FIG. 10 depicts an embodiment of the guidewire manipulation device 650 of FIG. 7 where the dimpled flange 710 has been engaged the protrusion surface 712. In this manner, the switch 702 has moved the coupler 700 forward to facilitate engagement of the surfaces 710 and 712. When the chuck 702 locks to the guidewire 102 and the rotary actuator is activated, the guidewire 102 rotates as shown in arrow 1002 and axially oscillates as represented by arrow 1000. The amount of linear oscillating motion could be variable (e.g., 0.5 mm to 5 mm) or could be set at a standard setting such as 1 mm.

Figure 11:
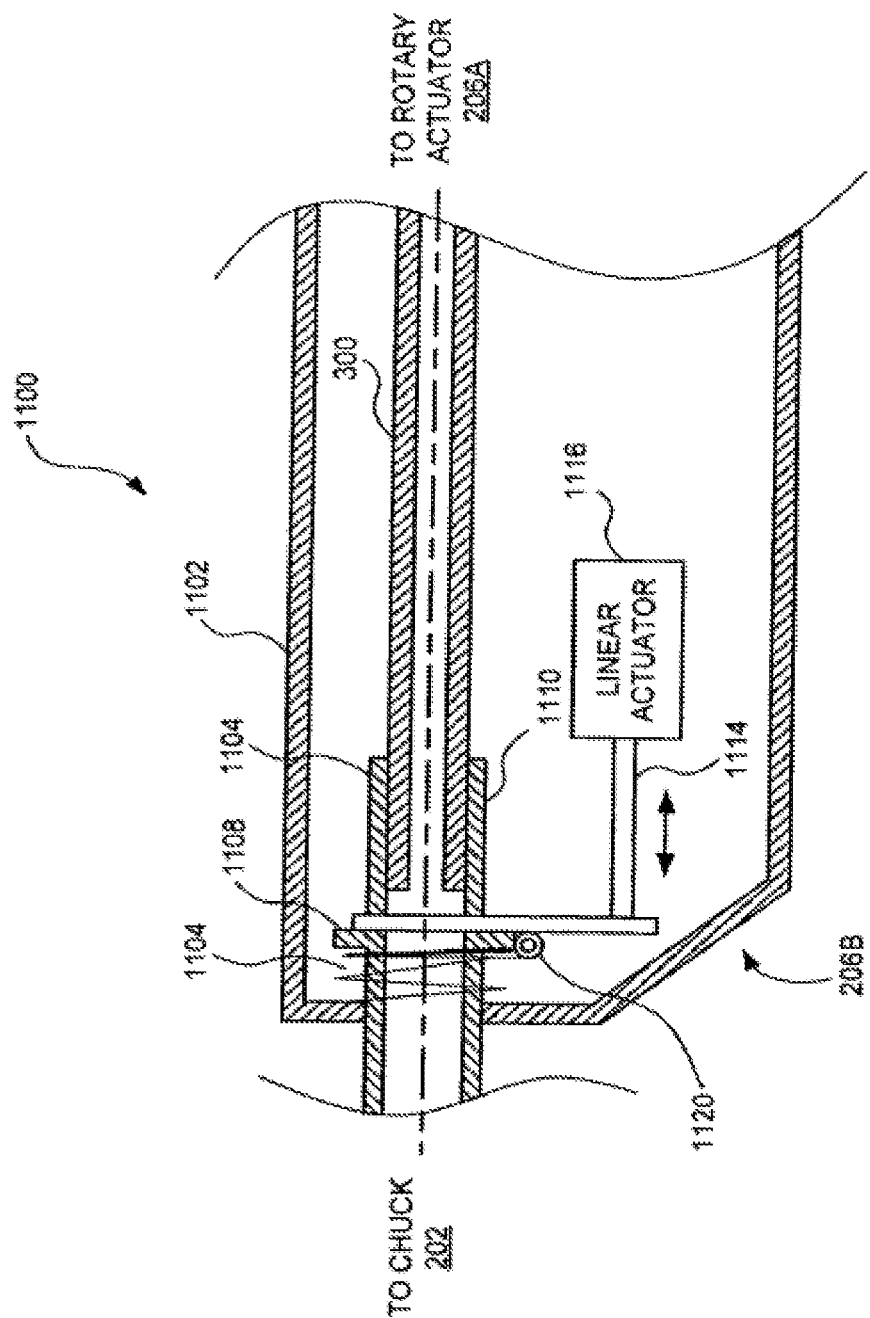
FIG. 11 depicts a partial, vertical cross-sectional view of another embodiment of a guidewire manipulation device for imparting axial motive force to a guidewire.

FIG. 11 depicts a vertical cross-sectional view of a portion of a guidewire manipulation device 1100. Device 1100 comprises an axial actuator 206B that can be selectively utilized without imparting rotational motion of the guidewire. As such, with this embodiment, the device 1100 selectively imparts to the guide wire; no motive force, rotary motive force, axial motive force, or axial and rotary motive force.

In one embodiment, the device 1100 comprises a linear actuator 1116 couple to a shaft of 1114 that interacts with a fulcrum 1112. The linear actuator 1116 imparts linear motion to one portion of the fulcrum 1112. The fulcrum is mounted upon a pivot point 1120 such that the fulcrum 1112 rotates about the pivot point 1120 as a linear motive force is applied to the fulcrum 1112. A second end of the fulcrum 1112 interacts with a coupler 1104. The coupler 1104, as with prior embodiments, has a splined surface that interacts with the axle 300 to impart rotational motion to the coupler, as needed. The coupler 1104 comprises a spring seat 1108. A spring 1106 is positioned between the housing 1102 and the spring seat 1108 to bias the coupler 1104 toward the axle 300. The fulcrum 1112 couples to the spring seat 1108 such that motion of the fulcrum 1112 axially moves the coupler 1104. In this manner, without any rotational motion the linear actuator 1116 imparts axial motion to the coupler and to guidewire 102 locked in the chuck 202.

In one embodiment, the linear actuator 1116 may be a solenoid, piezoelectric actuator, linear motor, rotary motor and ball screw or rack/pinion, and/or the like. In another embodiment, a hammer-drill type assembly may be used to impart axial for to the guidewire.

The controller 330 in a manner similar to that described for controlling the motor 328 of FIG. 3 may control the linear actuator 1116.

While the foregoing is directed to embodiments of the present invention, other and further embodiments of the invention may be devised without departing from the basic scope thereof, and the scope thereof is determined by the claims that follow.

What is claimed is:

1. A method for configuring a system for traversing an arterial occlusion in an artery comprising:
    providing a housing sized to fit in a palm of a user;
    providing a rotary actuator comprising:
        a manipulation member, moveably coupled to the housing, and
        an elongate drive tube rotationally disposed within the housing and configured to be rotated by thumb-activated movement of the manipulation member with respect to the housing, the drive tube having a first end and a second end and including a passage extending axially from the first end to the second end; and
    rotationally coupling a cylindrical member to the drive tube, the cylindrical member having a distal tip that is configured to be delivered to a location adjacent an arterial occlusion when the cylindrical member is coupled to the drive tube, such that thumb-activated movement of the manipulation member directly causes substantially only rotational movement of the cylindrical member, and wherein the rotating cylindrical member as a result of its rotational movement in turn effects a cyclic axial impact of the distal tip of the cylindrical member.

2. The method of claim 1, wherein the cyclic axial impact comprises a linear oscillation of between 0.5 mm and 5 mm.

3. The method of claim 2, wherein the linear oscillation is about 1 mm.

4. The method of claim 1, wherein the cyclic axial impact comprises a linear oscillation having a jack-hammer type motion.

5. The method of claim 1, wherein the cylindrical member comprises a guidewire.

6. The method of claim 1, wherein the manipulation member comprises a switch coupled to an exterior of the housing, the switch configured to control the rotational movement of the drive tube.

7. The method of claim 1, wherein the operation of rotationally coupling comprises rotationally coupling the cylindrical member to the drive tube by a chuck, the chuck configured to rotate with the drive tube.

8. The method of claim 1, wherein at least part of the cylindrical member is configured to reside within the passage from the first end to the second end.

9. The method of claim 1, wherein the housing includes a spring configured to facilitate axial movement of the cylindrical member with respect to the drive tube.

10. A method for using a system for traversing an arterial occlusion in an artery, the system having a housing sized to fit in a palm of a user, a rotary actuator including a manipulation member moveably coupled to the housing, and an elongate drive tube rotationally disposed within the housing and configured to be rotated by thumb-activated movement of the manipulation member with respect to the housing, the drive tube having a first end and a second end and including a passage extending axially from the first end to the second end, the method comprising:

rotationally coupling a cylindrical member to the drive tube, the cylindrical member having a distal tip that is configured to be delivered to a location in an artery when the cylindrical member is coupled to the drive tube;

positioning the distal tip of the cylindrical member adjacent to an arterial occlusion; and moving the manipulation member using at least a thumb to directly cause substantially only rotational movement of the cylindrical member, and wherein the rotating cylindrical member as a result of its rotational movement in turn effects a cyclic axial impact of the distal tip of the cylindrical member in relation to the arterial occlusion.

11. The method of claim 10, wherein the cyclic axial impact comprises a linear oscillation of between 0.5 mm and 5 mm.

12. The method of claim 11, wherein the linear oscillation is about 1 mm.

13. The method of claim 10, wherein the cyclic axial impact comprises a linear oscillation having a jack-hammer type motion.

14. The method of claim 10, wherein the cylindrical member comprises a guidewire.

15. The method of claim 10, wherein the manipulation member comprises a switch coupled to an exterior of the housing, the switch configured to control the rotational movement of the drive tube.

16. The method of claim 10, wherein the operation of rotationally coupling comprises rotationally coupling the cylindrical member to the drive tube by a chuck, the chuck configured to rotate with the drive tube.

17. The method of claim 10, wherein at least part of the cylindrical member is configured to reside within the passage from the first end to the second end.

18. The method of claim 10, wherein the housing includes a spring configured to facilitate axial movement of the cylindrical member with respect to the drive tube.

* * * * *